(12) United States Patent
Wei

(10) Patent No.: US 12,259,596 B2
(45) Date of Patent: Mar. 25, 2025

(54) OPHTHALMIC LENS HAVING EXTENDED DEPTH OF FIELD

(71) Applicant: MDCO Technology Limited, Hangzhou (CN)

(72) Inventor: Xin Wei, Hangzhou (CN)

(73) Assignee: MDCO TECHNOLOGY LIMITED, Hangzhou (CN)

( * ) Notice: Subject to any disclaimer, the term of this patent is extended or adjusted under 35 U.S.C. 154(b) by 637 days.

(21) Appl. No.: 17/568,332

(22) Filed: Jan. 4, 2022

(65) Prior Publication Data
US 2023/0047990 A1    Feb. 16, 2023

(30) Foreign Application Priority Data

Aug. 16, 2021    (CN) .......................... 202110936281.1

(51) Int. Cl.
*G02C 7/02* (2006.01)
(52) U.S. Cl.
CPC ...................... *G02C 7/02* (2013.01)
(58) Field of Classification Search
CPC .......... G02C 7/02; G02C 7/044; G02C 7/042; G02C 7/047; G02C 7/049; G02C 2202/24;
(Continued)

(56) References Cited

U.S. PATENT DOCUMENTS

2007/0182924 A1\* 8/2007 Hong ....................... G02C 7/06
   351/159.43
2010/0016961 A1\* 1/2010 Hong ..................... G02C 7/042
   351/159.41

(Continued)

FOREIGN PATENT DOCUMENTS

CN    102099729 A    6/2011
CN    111830731 A    10/2020

(Continued)

OTHER PUBLICATIONS

European Search Report issued Jul. 7, 2022 in European Application No. 22152317.8.

(Continued)

*Primary Examiner* — Darryl J Collins
*Assistant Examiner* — Matthew Y Lee
(74) *Attorney, Agent, or Firm* — Panitch Schwarze Belisario & Nadel LLP

(57) ABSTRACT

The present disclosure relates to an ophthalmic lens with an extended depth of field including an optical unit that includes a first surface and a second surface both centered by an optical axis and opposite to each other. At least one of the first and second surfaces is defined by a superposition of a base sag profile and a feature sag profile and includes in sequence a first zone, a second zone, and a third zone along a radial direction away from the optical axis. The first zone is designed as a freeform surface zone, and the second zone is designed as a phase transition zone. The ophthalmic lens enables patients to acquire a continuous range of vision from intermediate to far distances and also optimizes their far vision without visual interference, such that the resulting far vision correction is equivalent to that of existing monofocal ophthalmic lenses.

11 Claims, 7 Drawing Sheets

(58) Field of Classification Search
CPC .......... G02C 7/04; G02C 7/045; G02C 7/021;
G02C 7/048; G02C 7/028; G02C 7/061;
G02C 7/06; G02C 7/027; G02C 7/041;
G02C 7/063; A61F 2/1618; A61F 2/1613;
A61F 2002/1681; A61F 2/14; A61F
2/142; A61F 2/145; A61F 2/1451; A61F
2/147; A61F 2/16; A61F 2002/1696;
A61F 2230/0065; G02B 1/043; G02B
3/10
USPC ............. 351/159.1, 159.12, 159, 13, 14, 16,
351/159.2, 159.21, 15, 9.53, 159.54,
351/159.71, 159.72, 159.78, 159.79,
351/159.13, 159.14
See application file for complete search history.

(56) References Cited

U.S. PATENT DOCUMENTS

| | | | |
|---|---|---|---|
| 2015/0359625 A1* | 12/2015 | Argal | G02B 5/1876 623/6.24 |
| 2017/0245983 A1* | 8/2017 | Hong | A61F 2/1616 |
| 2019/0307553 A1* | 10/2019 | Hong | G02C 7/042 |
| 2021/0330452 A1* | 10/2021 | Choi | A61F 2/1618 |
| 2023/0301774 A1* | 9/2023 | Wang | G02C 7/042 |

FOREIGN PATENT DOCUMENTS

| | | |
|---|---|---|
| EP | 2637606 B1 | 9/2013 |
| EP | 2440962 B1 | 8/2014 |
| EP | 2993514 A1 | 3/2016 |
| JP | 2011-528451 A | 11/2011 |
| WO | 2010009254 A1 | 1/2010 |
| WO | 2021111821 A1 | 6/2021 |

OTHER PUBLICATIONS

Office Action issued Feb. 7, 2023 in Japanese Application No. 2022-005524 with English Translation.
Office Action issued Mar. 1, 2022 in Chinese Application No. 202110936281.1.
Extended European Search Report issued Nov. 7, 2023 in EP Application No. 23158898.9.

* cited by examiner

OPHTHALMIC LENS HAVING EXTENDED DEPTH OF FIELD

CROSS-REFERENCE TO RELATED PATENT APPLICATION

This application claims the benefit of and priority to Chinese Patent Application No. 202110936281.1 filed on Aug. 16, 2021, the entire disclosure of which is incorporated by reference herein.

TECHNICAL FIELD

The present disclosure relates to vision correction technologies, in particular to an ophthalmic lens with an extended depth of field.

BACKGROUND

Presbyopia is a condition that affects the accommodation of the eye. When a near object approaches a young and properly functioning eye, the effects of ciliary muscle contraction and zonule relaxation allow a lens of the eye to change shape and thereby increase its optical power (or focal power) and ability to focus at near distances. This accommodation enables the eye to focus and refocus at objects at various viewing distances.

The presbyopia typically develops as a person ages and is associated with a natural progressive loss of accommodation. In general, the presbyopic eye loses the ability to focus rapidly and easily on near objects at varying distances. The effects of presbyopia usually become noticeable after the age of 45 years. By age 65 years, the crystalline lens has often lost almost all of its elasticity and has only limited ability to change shape.

Along with the reduction in the accommodative ability of the eye, the aging may also cause clouding of the lens due to the formation of a cataract. The cataract may form in the hard central nucleus of the lens, in the soft peripheral cortical portion of the lens, or at the back of the lens, and may be treated by replacing the cloudy natural lens with an intraocular lens (IOL).

Monofocal IOLs are intended to provide distance vision correction at only one distance. The implantation of such monofocal IOLs may have limited accuracy in practice, and an inappropriate IOL power may leave patients with residual refraction post-surgery. Therefore, it may be necessary for the patients who have received IOL implants to also wear spectacles to achieve good far vision. At the very least, since a monofocal IOL that provides vision treatment at only one distance is typically configured to correct far vision, glasses are usually needed for good near (and sometimes intermediate) vision. The term "near vision" generally represents vision for objects at a distance of approximately 1 to 2 feet from the eye. The term "far vision" generally represents vision for objects at a distance of at least 6 feet or greater from the eye. The term "intermediate vision" generally represents vision for objects at a distance of approximately 2 feet to approximately 5 feet from the eye.

Various attempts have been made to address the limitations associated with the monofocal IOLs. For example, multifocal IOLs, each of which delivers in principle two foci (i.e., one near focus and one far focus) optionally with some degree of intermediate focus have been proposed. Such multifocal or bifocal IOLs are intended to provide good vision for two distances and include both refractive and diffractive multifocal IOLs. In some examples, the multifocal IOLs intended to correct vision for two distances may provide near add powers of about 3.0 or 4.0 Diopters.

For example, the multifocal IOLs may rely on diffractive optical surfaces to direct some of the light energy to different focal distances, thereby allowing the patients to see both far and near objects clearly. Multifocal ophthalmic lenses, including contact lenses, have also been proposed for the treatment of presbyopia without removing the natural crystalline lens.

Although the multifocal ophthalmic lenses have improved the quality of vision for many patients, further improvements are still beneficial. For example, some pseudophakic patients may experience undesirable visual effects (dysphotopsia), such as glare or halos. For example, if light from a distant point source is imaged on a retina through a far focus of the bifocal IOL, the near focus of the IOL may simultaneously superimpose a defocused image on the retina. The defocused image may manifest itself in a form of a ring of light around the in-focus image, which is thereby called a halo.

An ophthalmic lens with an extended depth of field can provide a certain patient with good vision over a continuous range of distances, while reducing or eliminating dysphotopisa. For example, an Extended Depth of Field (EDOF) IOL may achieve an effect of extending the optical depth of field for a patient by utilizing different optical technology (e.g. phase shift or diffraction). However, the existing EDOF IOLs, compared to monofocal IOLs, still need to be improved in terms of correction of far vision, especially in terms of visual disturbances.

SUMMARY

The present disclosure is intended to provide an improved ophthalmic lens with an extended depth of field, such as contact lenses, corneal inlays or onlays, or IOLs which may for example include phakic IOLs and piggyback IOLs (i.e., IOLs implanted in eyes with existing IOLs), to address at least the aforesaid and other technical problems of the prior art.

In an aspect, the present disclosure provides an ophthalmic lens with an extended depth of field, which includes an optical unit. The optical unit includes a first surface and a second surface that are both centered by an optical axis and are opposite to each other. At least one of the first surface and the second surface is defined by a superposition of a base sag profile and a feature sag profile and includes a first zone extending from the optical axis to a first radial boundary, a second zone extending from the first radial boundary to a second radial boundary, and a third zone extending from the second radial boundary to a circumference of the optical unit. The first zone is designed as a freeform surface zone, and the second zone is designed as a phase transition zone.

It should be noted that the aforesaid description is an overview of the present disclosure merely for facilitating better understanding of technical solutions of the present disclosure such that the present disclosure could be implemented in accordance with those described in the specification. Detailed description of the present disclosure will be illustrated below to make the aforesaid and other objects, features, and advantages of the present disclosure more clearly understood.

BRIEF DESCRIPTION OF THE DRAWINGS

For a more complete understanding of the present disclosure and its advantages, reference is now made to the following description in conjunction with the accompanying drawings in which same reference signs indicate same features. In the drawings.

Figure 1A:
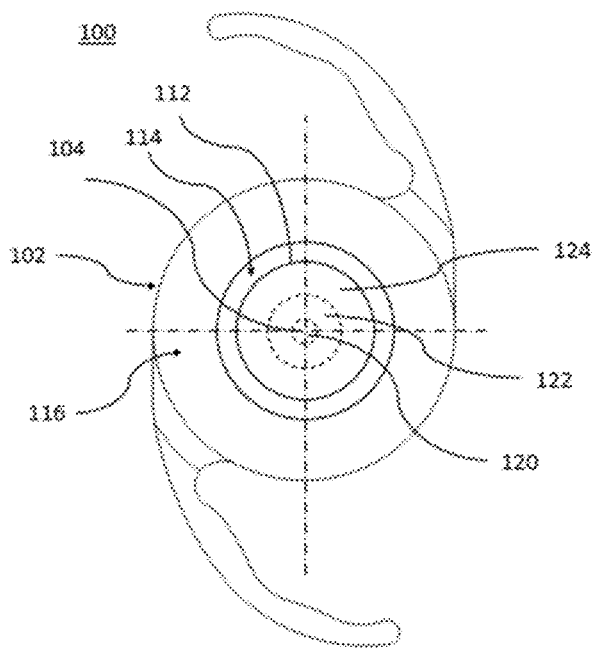
FIG. 1A shows a cross-sectional view of an ophthalmic lens according to some embodiments of the present disclosure.

It will be understood by those skilled in the art that the following accompanying drawings are for illustrative purposes only. These accompanying drawings are not intended to limit the scope of the present disclosure in any way.

DETAILED DESCRIPTION

It shall be understood that the present disclosure simplifies the accompanying drawings and description to illustrate the components of the present disclosure in a manner that is helpful for a clear understanding, and other components visible in a typical ophthalmic lens are not shown for the sake of clarity and brevity. Accordingly, one of ordinary skill in the art shall understand that there exist certain other components desirable and/or needed in implementing the present disclosure. Because such components are well known in the art and may not be conducive to a better understanding of the present disclosure, no description of such components is provided in the present disclosure. The present disclosure is intended to cover all changes and modifications based on components known to those skilled in the art.

An existing extended depth of field technology (such as the aforementioned EDOF IOLs) creates a single-elongated focal point corresponding to the range of vision covering both far and intermediate vision without a significant discretion of foci as in multifocal IOLs, and thereby can provide the patients with a continuous range of vision correction from far to intermediate distances. The known EDOF technology can be classified into two types. One type is to adopt diffraction technology as in multifocal technology, the principles and shortcomings of which are thus similar to those of multifocal correction technology. The other is to use phase shift technology and also have following two shortcomings. 1) Although this technology adopts the phase shift technology, there are at least two partitions with two completely different base profiles (e.g., sag (i.e., sagittal height) profiles). In addition, the energy distribution, although continuous, still needs to be optimized, and the corrected vision of the patient is still unsatisfactory when looking into the distance via a small aperture, thus there is still a certain gap compared with the effect of monofocal IOL far vision correction. 2) Since the phase shift zone is close to the optical center, the IOL based on this technology is more like a monofocal IOL in the case of a large aperture, which cause the reduced ability to correct intermediate vision and thereby fail to achieve the effect of extending the depth of field.

Compared to existing EDOF designs (e.g., EDOF IOL), the improved ophthalmic lens with an extended depth of field according to the present disclosure creates a single-elongated focal point corresponding to the range of vision covering both far and intermediate vision by a unique freeform surface combined with a phase transition technology. Specifically, parameters of the freeform surface are reasonably configured to overcome the problem in the prior art that two partitions have different base profiles, and relative positions and amplitudes for the phase transition with a higher degree of freedom compared with the existing phase shift technology are configured to not only ensure the correction of the far and intermediate vision of the patient under different apertures while optimizing the light energy distribution for the far vision of the patient. Thus, the ophthalmic lens according to the present disclosure enables patients to acquire correction over a continuous range of vision from intermediate to far distances and also optimizes their far vision without visual disturbances, such that the resulting far vision correction is equivalent to that of existing monofocal ophthalmic lenses (such as, IOL). According to embodiments of the present disclosure, the light energy is more effectively distributed for the range of vision from intermediate to far distances under different optical apertures, whereby the energy distribution for key frequency bands corresponding to far distances is optimized and enhanced under a premise of maintaining the continuity of energy distribution.

Embodiments of the present disclosure may advantageously provide an ophthalmic lens for vision correction (including, but not limited to, myopia, hyperopia, astigmatism, cataracts, and/or presbyopia) with an extended depth of field and enhanced vision. In some embodiments, the ophthalmic lens may include contact lenses, corneal inlays or covers, or artificial lenses (IOLs), which may for example include phakic IOLs and piggyback IOLs (i.e., IOLs implanted in eyes with existing IOLs). The ophthalmic lens according to the present disclosure is particularly useful for the treatment of presbyopia and cataracts in the middle-aged population.

Figure 1B:
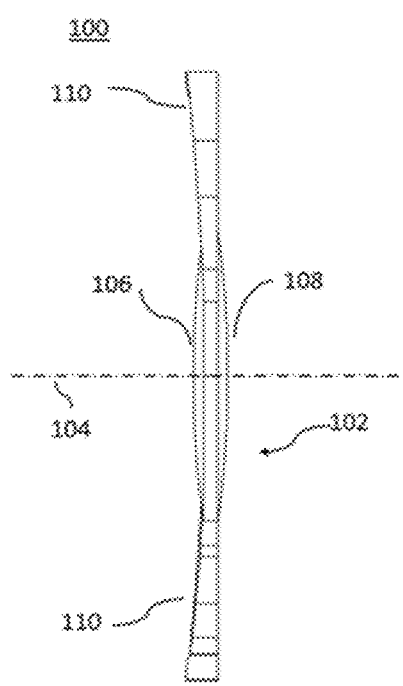
FIG. 1B shows a plan view of an ophthalmic lens according to some embodiments of the present disclosure.

FIG. 1A schematically shows a cross-sectional view of an ophthalmic lens 100 according to some embodiments of the present disclosure; and FIG. 1B schematically shows a plan view of an ophthalmic lens 100 according to some embodiments of the present disclosure. The ophthalmic lens 100 may include an optical unit 102. The optical unit 102 transmits (e.g., refracts) and focuses light received by the ophthalmic lens 100. As will be described in more detail below, the optical unit 102 may include a surface profile of one or more surfaces designed to refract and focus incident light to increase the depth of field and improve the visual acuity. For example, in some embodiments, the surface profile of the optical unit 102 may be designed such that the optical unit 102 can continuously focus incident light to increase the depth of field, thereby achieving a higher visual acuity (e.g., 20/25 vision) for the object vergence within a wide object distance range (e.g., the vergence within a range of at least about 0 to about 1.35 Diopters). In addition, in some embodiments, the surface profile of the optical unit 102 may be designed such that the images are substantially coaxial and have a substantially similar magnitude to reduce the presence of ghost images.

As shown in FIG. 1A and FIG. 1B, the exemplary ophthalmic lens 100 may further include a haptic component 110. In some embodiments, one or more haptic components 110 may be included to stabilize the ophthalmic lens 100 in and attach the ophthalmic lens 100 to the eye. For example, a plurality of haptic components 110 are provided to surround the optical unit 102 to affix the optical unit 102 in place when implanted in the eye. In some embodiments, the haptic component 110 is provided to stabilize the optical unit 102 in the eye, such that an optical axis of the optical unit 102 is disposed along a central optical axis of the eye. In such embodiments, the stability of the wavefront of the optical unit 102 in the eye may be provided by the haptic component 110. In some embodiments, the ophthalmic lens 100 and, in particular, the haptic member 110 are provided to be implanted outside a capsular bag, and may, for example, be designed to be implanted in front of a natural lens for a phakic IOL. For example, the phakic IOL may be provided to be implanted between the iris and the natural lens. Although two haptic components 110 as shown are in a form of wings, there is no particular limitation on the shape, size, and number of the haptic components 110. In some embodiments, the ophthalmic lens is provided for implantation into the capsular bag after removing the natural lens. Such an ophthalmic lens may have a haptic components 110 which is in a shape, size, and/or number suitable for providing secure placement and orientation within the capsular bag after implantation.

As shown in FIG. 1B, the optical unit 102 includes a first surface 106 and a second surface 108 that are opposite to each other. For example, the first surface 106 and the second surface 108 are both centered by the optical axis 104, and one of the first surface 106 and the second surface 108 is an anterior surface, with the other being a posterior surface.

In some embodiments, the first surface 106 includes: a first zone 112 extending from the optical axis 104 to the first radial boundary; a second zone 114 extending from the first radial boundary to the second radial boundary; and a third zone 116 extending from the second radial boundary to a circumference of the optical unit 102. The first zone 112 is designed as a freeform surface zone, the second zone 114 is designed as a phase transition zone, and the third zone 116 is designed as a peripheral optical zone. The surface profile of the first surface 106 is defined by the superposition of the base sag profile and the feature sag profile. For example, the base sag profile may be spherical or aspheric.

Although the first zone 112, the second zone 114, and the third zone 116 described above are illustrated and described as being disposed on the first surface 106 of the optical unit 102, the present disclosure contemplates that the first zone 112, the second zone 114, and the third zone 116 may additionally or alternatively be disposed on a second surface 108 of the optical unit 102, such that a similar light wave phase modulation effect is produced. In addition, the optical unit 102 determines a reference focal length of the ophthalmic lens, which typically needs to correspond to the patient's distance vision correction. However, the additional focal length of the ophthalmic lens may be defined relative to the reference focal length depending on the situation, e.g., depending on the dominant and non-dominant eyes to thereby improve the overall vision of both eyes.

As a particular embodiment, the surface profile of the first surface 106 may be described as a following equation (1):

$$Z(r) = Z_{base}(r) + Z_{feature}(r) \quad (1)$$

where $Z(r)$ represents a sag profile of the first surface 106, $Z_{base}(r)$ represents the base sag profile, $Z_{feature}(r)$ represents the feature sag profile, and r represents a radial distance from the optical axis 104.

$Z_{base}(r)$ and $Z_{feature}(r)$ may be described as following equations (2) and (3), respectively:

$$Z_{base}(r) = \frac{cr^2}{1 + \sqrt{1 - (1+k)c^2 r^2}} + a_4 r^4 + a_6 r^6 \quad (2)$$

$$Z_{feature}(r) = \begin{cases} Z_{112}(r), & 0 < r \le r112 \\ Z_{114}(r), & r112 < r \le r114 \\ Z_{116}(r), & r114 < r \le r_{oz} \end{cases} \quad (3)$$

where c represents a base curvature of the first surface 106; k represents a conic constant; $a_4$ and $a_6$ represent a fourth order coefficient and a sixth order coefficient, respectively; $Z_{112}(r)$, $Z_{114}(r)$ and $Z_{116}(r)$ represent the feature sag profiles corresponding to the first zone 112, the second zone 114 and the third zone 116, respectively; and r112, r114 and $r_{oz}$ represent radial distances from the optical axis 104 to the first radial boundary, the second radial boundary, and the circumference of the optical unit 102, respectively.

Although the equation (2) describes the base sag profile of the aspheric surface in general, the equation (2) may be configured to describe the spherical surface by choosing k, $a_4$ and $a_6$ to be all zero.

In some embodiments, the first zone 112 as a freeform surface zone may include an inner region 120, a middle region 122, and an outer region 124 along a radial direction away from the optical axis 104. In the feature sag profile of the first zone 112 (i.e., without the contribution of the base sag profile), the sag of the inner region 120 is constant, sag of the middle region 122 increases as per a power series along a radial direction away from the inner region 120, and the sag of the outer region 124 increases linearly.

As a particular embodiment, $Z_{112}(r)$ corresponding to the feature sag profile of the first zone 112 may be a continuous curve and may be expressed as the following equation (4a):

$$Z_{112}(r) = \begin{cases} 0, & 0 < r \le r_{120} \\ k_{122\_4} r^4 + k_{122\_3} r^3 + k_{122\_2} r^2 + k_{122\_1} r^1 + k_{122\_0}, & r_{120} < r \le r_{122} \\ k_{124\_1} r^1 + k_{124\_0}, & r_{122} < r \le r112 \end{cases} \quad (4a)$$

where $r_{120}$ and $r_{122}$ represent radial distances from the optical axis 104 to outer peripheral boundaries of the inner region 120 and the middle region 122, respectively; $k_{122\_4}$, $k_{122\_3}$, $k_{122\_2}$, $k_{122\_1}$, and $k_{122\_0}$ represent polynomial coefficients of the feature sag profile corresponding to the middle region 122; and $k_{124\_1}$ and $k_{124\_0}$ represent linear coefficients of the feature sag profile corresponding to the outer region 124, with the $k_{122\_0}$ and $k_{124\_0}$ enabling the function continuity of $Z_{112}(r)$.

Figure 2:
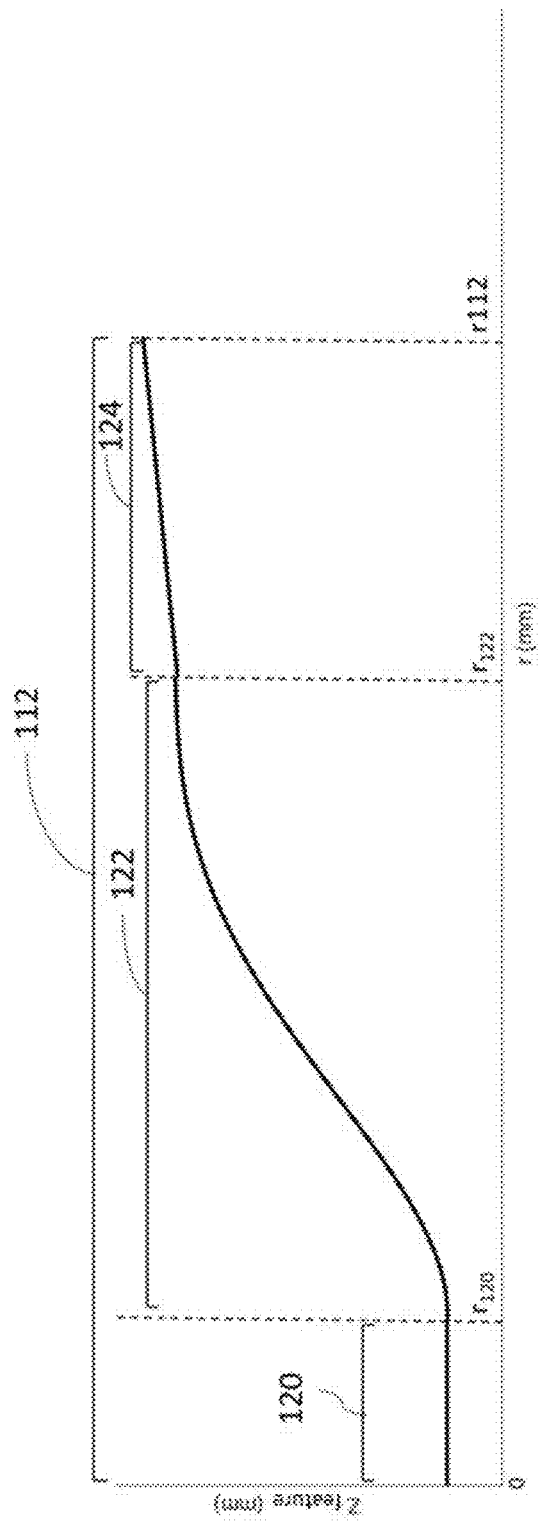
FIG. 2 shows a graph of a feature sag profile of a first zone in an optical unit of an ophthalmic lens according to some embodiments of the present disclosure.

FIG. 2 shows a graph of a feature sag profile of a first zone 112 in an optical unit of an ophthalmic lens according to some embodiments of the present disclosure. The horizontal axis represents a radial distance from the optical axis 104, and the vertical axis represents a feature sag at the radial distance (i.e., without the contribution of the base sag profile).

Preferably, the radial distance $r_{120}$ (e.g., a boundary radius) of the peripheral boundary of the inner region 120 from the optical axis 104 is in a range of 0.15 mm to 0.35 mm. Preferably, the power increase in the feature sag of the middle region 122 produces an optical power greater than 0 D (Diopter) and less than 1 D, and the radial distance $r_{122}$ of the peripheral boundary of the middle region 122 from the optical axis 104 is in the range of 0.85 mm to 1.15 mm. Preferably, the linear increase in the feature sag of the outer region 124 produces an optical power greater than −0.5 D and less than +0.5 D, and the radial distance $r_{112}$ of the outer peripheral boundary of the outer region 124 from the optical axis 104 is in the range of 1.2 mm to 1.5 mm.

As an alternative or optional embodiment, the feature sag profile of the first zone 112 is not configured by partition (e.g., inner, middle, and outer regions as described above), but is defined by polynomial fitting as a whole or in the form of a spline curve by fixing key nodes, provided that the aforesaid features are substantially satisfied.

As a particular embodiment, $Z_{112}(r)$ corresponding to the feature sag profile of the first zone 112 may be overall expressed as the following equation (4b):

$$Z_{112}(r) = \Sigma_{n=0}^{N} k_{112\_n} r^n, \quad 0 < r \leq r_{112} \tag{4b}$$

where $k_{112\_n}$ represents a polynomial coefficient of the feature sag profile defining the first zone 112, and N represents a polynomial coefficient required to achieve the feature sag profile of the first zone 112.

In some embodiments, the second zone 114 as a phase transition zone may include at least one stepped portion. In the feature sag profile of the second zone 114 (i.e., without the contribution of the base sag profile), the sag of each stepped portion increases in a radial direction away from the optical axis 104.

As a particular embodiment, $Z_{114}(r)$ corresponding to the feature sag profile of the second zone 114 may be expressed as the following equation (5):

$$Z_{114\_i}(r) = \frac{h_i(r - r_i)}{(r_{i+1} - r_i)} + z_i, \quad i = 1, 2, 3 \ldots \tag{5}$$

where $Z_{114\_i}(r)$ represents a feature sag profile defining an $i^{th}$ stepped portion from the at least one stepped portion; hi represents a feature sag difference between an outer peripheral boundary and an inner peripheral boundary of the $i^{th}$ stepped portion; $r_i$ represents a radial distance from the inner peripheral boundary of the $i^{th}$ stepped portion to the optical axis 104; and $z_i$ represents a feature sag of the inner peripheral boundary of the $i^{th}$ stepped portion. It shall be noted that $r_i$ is equal to r112, and $r_{(i+1)}$ is equal to r114 for the last stepped portion (i.e., the outermost stepped portion with the largest i). Preferably, in order to ensure continuity between the inner peripheral boundary of the first stepped portion of the second zone 114 (i.e., the innermost stepped portion with i being 1) and the first zone 112, the feature sag $z_1$ of the inner peripheral boundary of the of the first stepped portion may be substantially the same as the feature sag of the first zone 112 at the first radial boundary (i.e., at a distance r112 from the optical axis 104).

Figure 3:
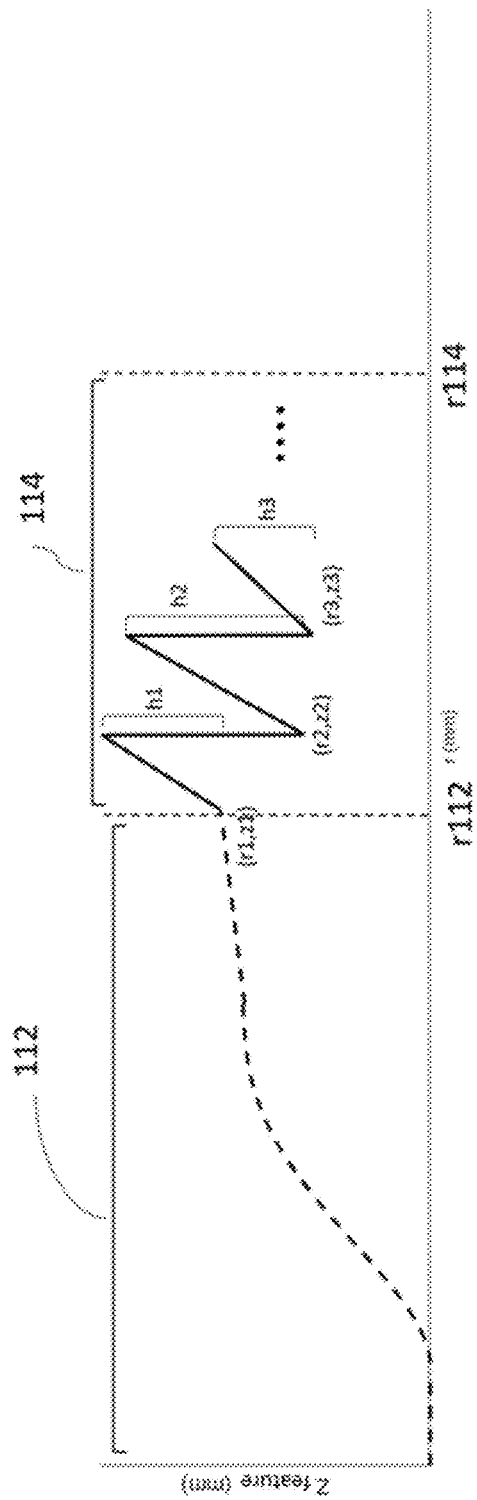
FIG. 3 shows a graph of a feature sag profile of a second zone in an optical unit of an ophthalmic lens according to some embodiments of the present disclosure.

FIG. 3 shows a graph of a feature sag profile of a second zone 114 in an optical unit of an ophthalmic lens according to some embodiments of the present disclosure. The horizontal axis represents a radial distance from the optical axis 104, and the vertical axis represents a feature sag at the radial distance (i.e., without the contribution of the base sag profile).

Preferably, the number of stepped portions of the second zone 114 is in the range of 1 to 4. Preferably, the radial width of the stepped portion (i.e., $r_{i+1} - r_i$) is in the range of 0.1 mm to 0.3 mm, and the optical path difference of the step height (i.e., $h_i$) is in the range of 0.1 wave to 0.5 wave at the designed wavelength. Preferably, the radial distance r114 of the second radial boundary from the optical axis 104 is in the range of 1.5 mm to 2.0 mm.

In some embodiments, the feature sag profile of the third zone 116, which is the peripheral optical zone, is substantially constant.

As a particular embodiment, $Z_{116}(r)$ corresponding to the feature sag profile of the third zone 116 may be expressed as the following equation (6):

$$Z_{116}(r) = C, \quad r114 < r \leq r_{oz} \tag{6}$$

where C represents a constant.

As an example, C may be 0. As another example, in order to ensure continuity between the third zone 116 and the second zone 114, C may be substantially the same as the feature sag of the second zone 114 at the second radial boundary (i.e., at a distance r114 from the optical axis 104).

Figure 4:
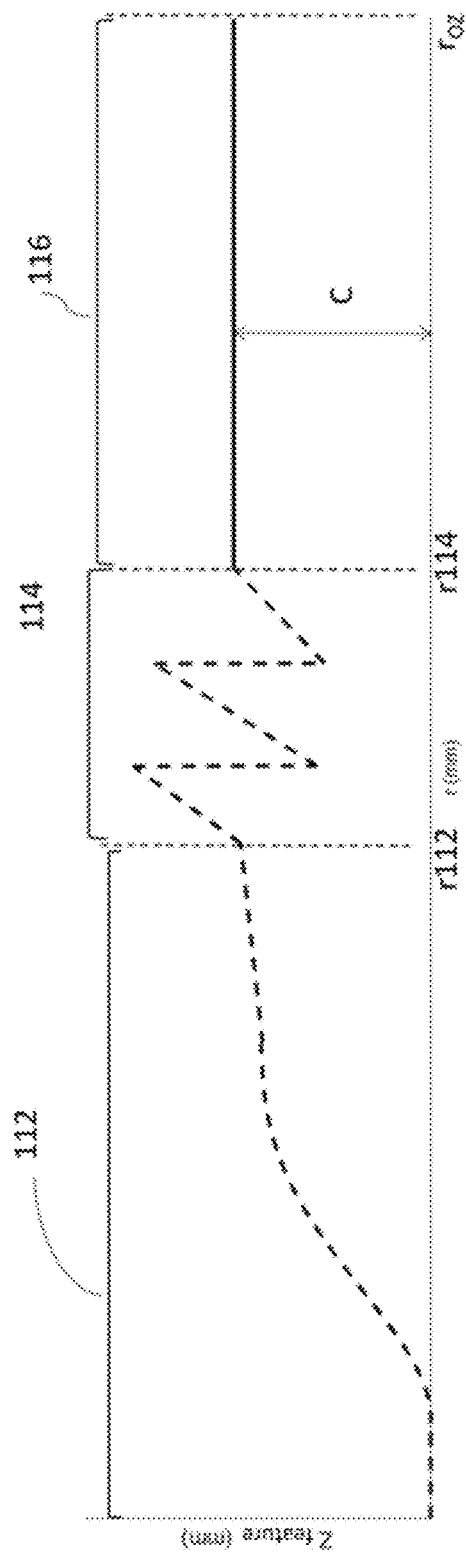
FIG. 4 shows a graph of a feature sag profile of a third zone in an optical unit of an ophthalmic lens according to some embodiments of the present disclosure.

FIG. 4 shows a graph of a feature sag profile of a third zone 116 in an optical unit of an ophthalmic lens according to some embodiments of the present disclosure. The horizontal axis represents a radial distance from the optical axis 104, and the vertical axis represents a feature sag at the radial distance (i.e., without the contribution of the base sag profile).

Preferably, the radial distance $r_{oz}$ to the peripheral boundary of the third zone 116, i.e., the circumference of the optical unit 102, from the optical axis 104 is in a range of 2.5 mm to 4.0 mm.

The improved ophthalmic lens with an extended depth of field according to the present disclosure may produce a delay in the phase distribution of light waves in space by an optical unit having at least some of the aforementioned features, such that each subwave of different phases in the light waves distributed in space generates interference, thereby achieving the effect of extending the depth of field by rational distribution of light energy for the range of vision from far to intermediate distances.

The experimental examples will be described in detail below in conjunction with specific examples of the present disclosure and comparative examples for performance comparison.

An example of an improved ophthalmic lens with an extended depth of field according to the present disclosure is designed and prepared based on the parameters illustrated in Table 1 below, where only one surface employs a superposition of the base sag profile and the feature sag profile based on the parameters in Table 1 below.

TABLE 1

| Parameters | Values |
| --- | --- |
| Lens material refractive index | 1.55 |
| r112 | 1.22 mm |
| r114 | 1.90 mm |
| $r_{oz}$ | 3.00 mm |
| $r_{120}$ | 0.19 mm |
| $r_{122}$ | 1.05 mm |
| $k_{122\_4}$ | 0.00086632 mm$^{-3}$ |

TABLE 1-continued

| Parameters | Values |
|---|---|
| $k_{122\_3}$ | −0.00369424 mm$^{-2}$ |
| $k_{122\_2}$ | 0.00492636 mm$^{-1}$ |
| $k_{122\_1}$ | −0.00129371 |
| $k_{122\_0}$ | 0.00009217 mm |
| $k_{124\_1}$ | 0 |
| $k_{124\_0}$ | 0.00094157 mm |
| $r_1$ | 1.22 mm |
| $z_1$ | 0.37 wave |
| $h_1$ | 0.09 wave |
| $r_2$ | 1.505 mm |
| $z_2$ | 0.26 wave |
| $h_2$ | 0.23 wave |
| $r_3$ | 1.71 mm |
| $z_3$ | 0.24 wave |
| $h_3$ | 0.15 wave |
| $r_4$ | 1.90 mm |
| c | 1/15 mm$^{-1}$ |
| k | 0.21 |
| $a_4$ | 0.0016 |
| $a_6$ | 0.000078 |

Figure 5:
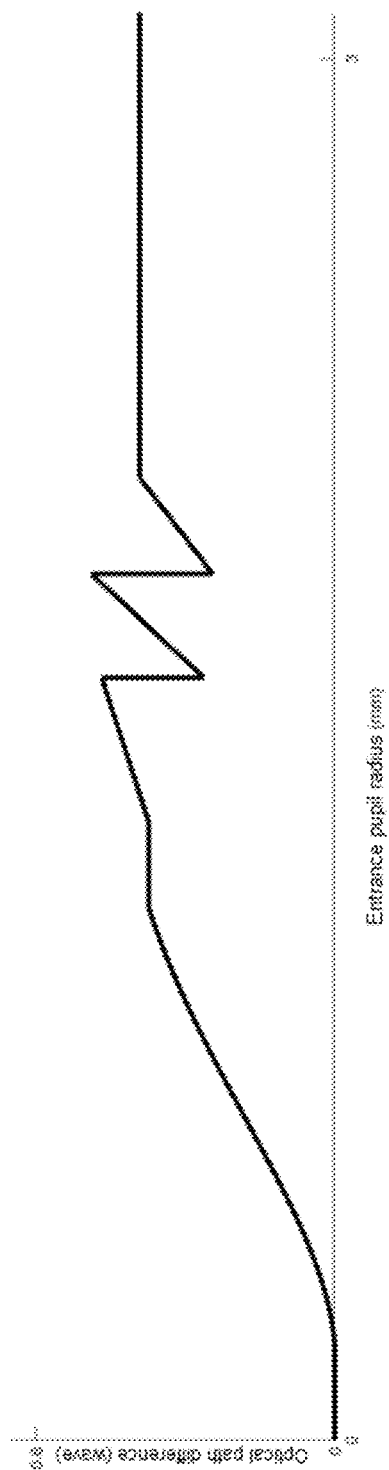
FIG. 5 shows a graph of a wavefront aberration distribution in a first surface of an optical unit of an ophthalmic lens according to some embodiments of the present disclosure.

FIG. 5 shows a schematic diagram of wavefront aberration vector diameter of an ophthalmic lens according to the aforesaid example in a pupillary plane of the eyeball.

The existing monofocal ophthalmic lens prepared as a comparative example is essentially the same as the ophthalmic lens according to the aforesaid example, except for that a corresponding surface employs only the same base sag profile (that is, parameters, such as the lens material refractive index, $r_{oz}$, c, k, a4, a6, etc., are the same) as in the example without the feature sag profile.

Figure 6A:
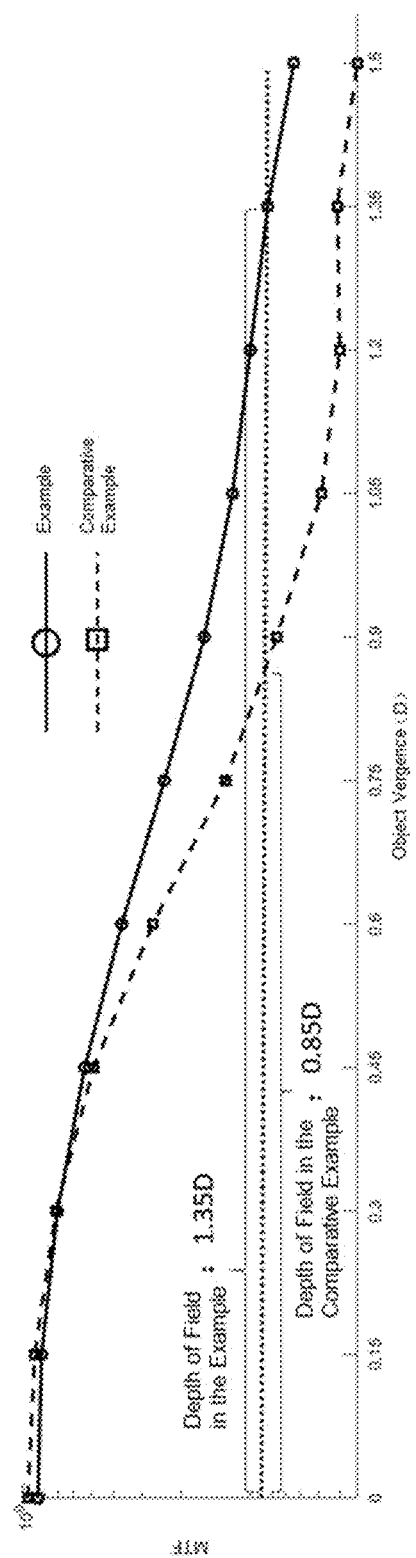
FIG. 6A shows respective graphs of modulation transfer function (MTF) of an ophthalmic lens according to an example of the present disclosure and a conventional ophthalmic lens taken as a comparative example.
Figure 6B:
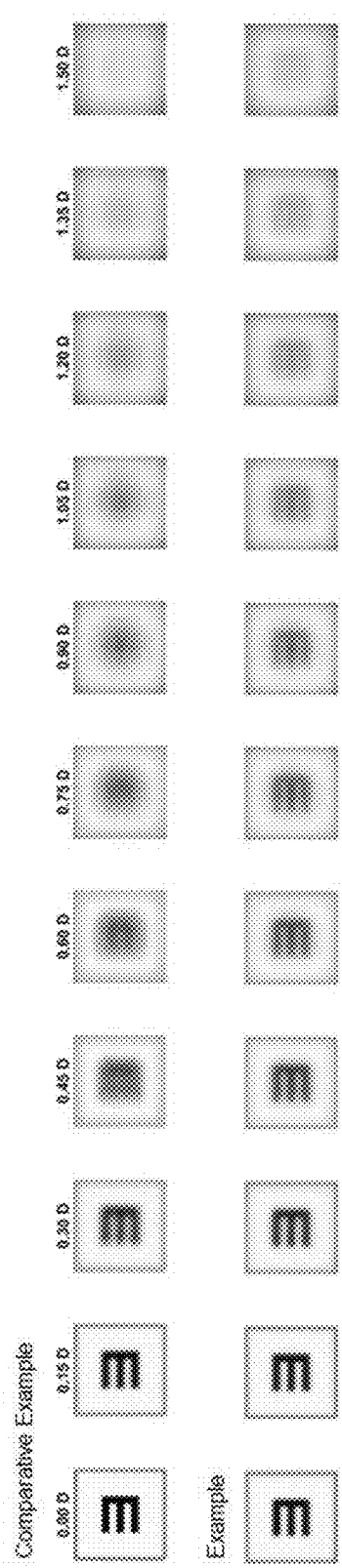
FIG. 6B shows actual images captured during experiments based on FIG. 6A for an ophthalmic lens according to the example of the present disclosure and the conventional ophthalmic lens taken as the comparative example.

In order to confirm the performance improvement of the ophthalmic lens with an extended depth of field according to the example of the present disclosure over the existing monofocal ophthalmic lens taken as a comparative example, modulation transfer function (MTF) are obtained for different object vergences to acquire images, the results of which are shown in FIG. 6A and FIG. 6B.

The horizontal axis of FIG. 6A represents the object vergence in Diopter, which is an inverse of the object distance. For example, 0 Diopter corresponds to an object distance at infinity, 1 Diopter corresponds to an object distance of 1 meter, and 1.5 Diopter corresponds to an object distance of approximately 0.67 meters. The vertical axis of FIG. 6A indicates the MTF value measured for the corresponding object vergence, and the higher the value, the higher the imaging quality. As seen in FIG. 6A, for a given MTF threshold, a depth of field of up to 1.35 D is acquired with the ophthalmic lens according to the example of the present disclosure, whereas the existing ophthalmic lens of the comparative example merely acquires a depth of field of only about 0.85 D. Thus, the depth of field of the ophthalmic lens according to the example of the present disclosure is increased by about 58% compared to the existing ophthalmic lens of the comparative example. FIG. 6B employs a letter E (opening leftward) with a size corresponding to 20/32 (−0.6) in the vision table. As seen in FIG. 6B, in the images acquired with the ophthalmic lens according to the example of the present disclosure, the opening direction of the letter E can be distinguished and identified even at an object vergence of 1.35 D. In the images acquired with the existing ophthalmic lens of the comparative example, the opening direction of the letter E cannot be distinguished and identified at an object vergence of 0.75 D or more. Thus, compared with the ophthalmic lens of the comparative example, the ophthalmic lens according to the example of the present disclosure not only can significantly extend the depth of field of the patient, but also has no significant difference in the imaging quality, especially clarity and contrast, when looking into the distance (e.g., 0 D).

The terms "approximately" and "substantially" herein denote an amount that is equal to or close to the stated amount (e.g., an amount that still performs the desired function or achieves the desired result). For example, unless otherwise stated, the terms "about" and "substantially" may refer to the amount within (e.g., above or below) 10%, within (e.g., above or below) 5%, within (e.g., above or below) 1%, within (e.g., above or below) 0.1%, or within (e.g., above or below) 0.01% of the stated amount.

Various embodiments of the present disclosure have been described herein. Although the present disclosure has been described with reference to specific embodiments, this specification is only intended to illustrate rather than limit the present disclosure. Those of ordinary skill in the art may envisage various modifications and applications without departing from the basic concept and scope of the present disclosure.

What is claimed is:

1. An ophthalmic lens with an extended depth of field, comprising an optical unit including a first surface and a second surface that are both centered by an optical axis and are opposite to each other, wherein at least one of the first surface and the second surface is defined by a superposition of a base sag profile and a feature sag profile and comprises:

a first zone extending from the optical axis to a first radial boundary;

a second zone extending from the first radial boundary to a second radial boundary; and a third zone extending from the second radial boundary to a circumference of the optical unit;

wherein the first zone is designed as a freeform surface zone, and the second zone is designed as a phase transition zone, wherein the first zone comprises in sequence an inner region, a middle region and an outer region along a radial direction away from the optical axis, wherein in the feature sag profile corresponding to the first zone, a feature sag of the inner region is constant, a feature sag of the middle region increases as per a non-linear polynomial along a radial direction away from the inner region, and a feature sag of the outer region increases linearly.

2. The ophthalmic lens according to claim 1, wherein the at least one surface is defined by:

$$Z(r) = Z_{base}(r) + Z_{feature}(r),$$

wherein Z (r) represents a sag profile of the at least one surface, $Z_{base}$ (r) represents the base sag profile, $Z_{feature}$ (r) represents the feature sag profile, and r represents a radial distance from the optical axis, $$Z_{base}(r) = \frac{cr^2}{1 + \sqrt{1 - (1+k)c^2 r^2}} + a_4 r^4 + a_6 r^6,$$

$$Z_{feature}(r) = \begin{cases} Z_{112}(r), & 0 < r \leq r112 \\ Z_{114}(r), & r112 < r \leq r114 \\ Z_{116}(r), & r114 < r \leq r_{oz} \end{cases}$$

wherein c represents a base curvature of the at least one surface; k represents a conic constant; $a_4$ and $a_6$ represent a fourth order coefficient and a sixth order coefficient, respectively;

$Z_{112}(r)$, $Z_{114}(r)$ and $Z_{116}(r)$ represent feature sag profiles corresponding to the first zone, the second zone and the third zone, respectively; and r112, r114 and $r_{oz}$ represent radial distances from the optical axis to the first radial boundary, the second radial boundary, and the circumference of the optical unit, respectively, wherein r112 is in a range of 1.2 mm to 1.5 mm, r114 is in a range of 1.5 mm to 2.0 mm, $r_{oz}$ is in a range of 2.5 mm to 4.0 mm, c is 1/15 mm−1, k is 0.21, $a_4$ is 0.0016, and $a_6$ is 0.000078.

3. The ophthalmic lens according to claim 2, wherein the first zone comprises in sequence an inner region, a middle region and an outer region along a radial direction away from the optical axis, and $$Z_{112}(r) = \begin{cases} 0, & 0 < r \leq r_{120} \\ k_{122\_4}r^4 + k_{122\_3}r^3 + k_{122\_2}r^2 + k_{122\_1}r^1 + k_{122\_0}, & r_{120} < r \leq r_{122} \\ k_{124\_1}r^1 + k_{124\_0}, & r_{122} < r \leq r112 \end{cases}$$

wherein $r_{120}$ and $r_{122}$ represent radial distances from the optical axis to outer peripheral boundaries of the inner region and the middle region, respectively; $k_{122\_4}$, $k_{122\_3}$, $k_{122\_2}$, $k_{122\_1}$, and $k_{122\_0}$ represent polynomial coefficients of the feature sag profile corresponding to the middle region; and $k_{124\_1}$ and $k_{124\_0}$ represent linear coefficients of the feature sag profile corresponding to the outer region, with $k_{122\_0}$ and $k_{124\_0}$ enabling continuity of $Z_{112}(r)$, wherein $r_{120}$ is in a range of 0.15 mm to 0.35 mm, $r_{122}$ is in a range of 0.85 mm to 1.15 mm, $k_{122\_4}$ is 0.00086632 mm−3, $k_{122\_3}$ is −0.00369424 mm−2, $k_{122\_2}$ is 0.00492636 mm−1, $k_{122\_1}$ is −0.00129371, $k_{122\_0}$ is 0.00009217 mm, $k_{124\_1}$ is 0 and $k_{124\_0}$ is 0.00094157 mm.

4. The ophthalmic lens according to claim 3, wherein an optical power generated by the middle region is greater than 0D and less than 1D, and an optical power generated by the outer region is greater than −0.5D and less than +0.5D.

5. The ophthalmic lens according to claim 2, wherein the second zone comprises at least one stepped portion, and $$Z_{114\_i}(r) = \frac{h_i(r - r_i)}{(r_{i+1} - r_i)} + z_i, \quad i = 1, 2, 3 \ldots,$$

wherein $Z_{114\_i}(r)$ represents a feature sag profile corresponding to an $i^{th}$ stepped portion from the at least one stepped portion; $h_i$ represents a feature sag difference between an outer peripheral boundary and an inner peripheral boundary of the $i^{th}$ stepped portion; $r_i$ represents a radial distance from the inner peripheral boundary of the $i^{th}$ stepped portion to the optical axis; and $z_i$ represents a feature sag of the inner peripheral boundary of the $i^{th}$ stepped portion, wherein the second zone comprises three stepped portions each having a radial width in a range of 0.1 mm to 0.3 mm and $h_i$ in a range of 0.1 wave to 0.5 wave, and $z_1$, $z_2$ and $z_3$ are 0.37 wave, 0.26 wave and 0.24 wave, respectively.

6. The ophthalmic lens according to claim 5, wherein the feature sag $z_i$ of the inner peripheral boundary of the first stepped portion is essentially the same as the feature sag of the first zone at the first radial boundary.

7. The ophthalmic lens according to claim 2, wherein $Z_{116}(r) = C, r114 < r \leq r_{oz}$, wherein C represents a constant that is equal to the feature sag of the second zone at the second radial boundary.

8. The ophthalmic lens according to claim 1, wherein the second zone comprises at least one stepped portion, and wherein in the feature sag profile corresponding to the second zone, the sag of each stepped portion increases along a radial direction away from the optical axis.

9. The ophthalmic lens according to claim 8, wherein the second zone comprises one to four stepped portions.

10. The ophthalmic lens according to claim 8, wherein the at least one stepped portion each has a radial width in a range of 0.1 mm to 0.3 mm and a height in a range of 0.1 wave to 0.5 wave; and the second radial boundary has a radial distance from the optical axis in a range of 1.5 mm to 2.0 mm.

11. The ophthalmic lens according to claim 1, wherein the feature sag profile corresponding to the third zone is substantially constant.

* * * * *